United States Patent [19]

Russ et al.

[11] Patent Number: 4,545,983
[45] Date of Patent: * Oct. 8, 1985

[54] METHOD FOR MAKING COSMETIC PENCILS

[75] Inventors: Julio G. Russ, Germantown; Donna L. Barrom, Arlington, both of Tenn.

[73] Assignee: Plough, Inc., Memphis, Tenn.

[*] Notice: The portion of the term of this patent subsequent to May 17, 2000 has been disclaimed.

[21] Appl. No.: 472,543

[22] Filed: Mar. 7, 1983

Related U.S. Application Data

[63] Continuation-in-part of Ser. No. 296,386, Aug. 26, 1981, Pat. No. 4,383,875.

[51] Int. Cl.$^4$ .................. A61K 7/21; A61K 7/25; B65B 7/28
[52] U.S. Cl. ........................... 424/63; 424/64; 424/DIG. 5; 156/69; 156/153; 156/154; 156/187; 156/192; 156/250; 156/264; 401/88; 401/98; 53/440; 29/415; 132/79 C; 132/88.7
[58] Field of Search .............. 401/98, 49, 88; 132/88.7, 79 C; 424/63, 64, DIG. 5; 156/69, 153, 154, 187, 192, 250, 264; 106/224, 230, 19, 245, 268; 53/440; 29/411, 415

[56] References Cited

U.S. PATENT DOCUMENTS

| | | | |
|---|---|---|---|
| 2,419,526 | 4/1947 | Anderson | 401/75 |
| 3,088,876 | 5/1963 | Buth | 424/63 |
| 3,106,908 | 10/1963 | Gretz | 401/62 |
| 3,211,618 | 10/1965 | Kambersky | 424/63 |
| 4,334,546 | 6/1982 | Floyd et al. | 401/49 |

FOREIGN PATENT DOCUMENTS

| | | | |
|---|---|---|---|
| 48571 | 3/1982 | European Pat. Off. | 401/49 |
| 1948351 | 5/1970 | Fed. Rep. of Germany | 132/88.7 |
| 2540877 | 9/1976 | Fed. Rep. of Germany | 424/63 |
| 2027343 | 2/1980 | United Kingdom | |

*Primary Examiner*—Robert J. Warden
*Assistant Examiner*—Shawn P. Foley
*Attorney, Agent, or Firm*—Thomas D. Hoffman; Warrick E. Lee; Gerald S. Rosen

[57] ABSTRACT

A method for making a cosmetic pencil having a lead of solvent-based cosmetic composition.

The leads are packaged in an airtight container, such as a plastic bag and stored in a freezer at a temperature below approximately 0° for approximately 12 to 168 hours. The leads are then stored at room temperature for at least two hours and unpackaged. Then the leads are encased in grooved slats to form an assembly which is wrapped with airtight wrapping.

7 Claims, 4 Drawing Figures

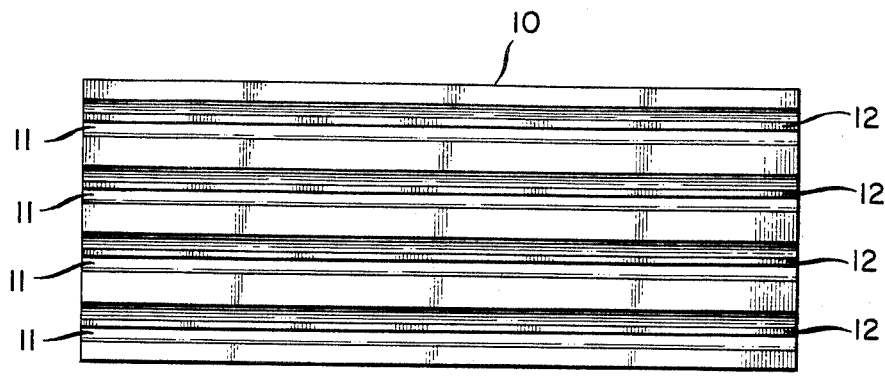
FIG. 2
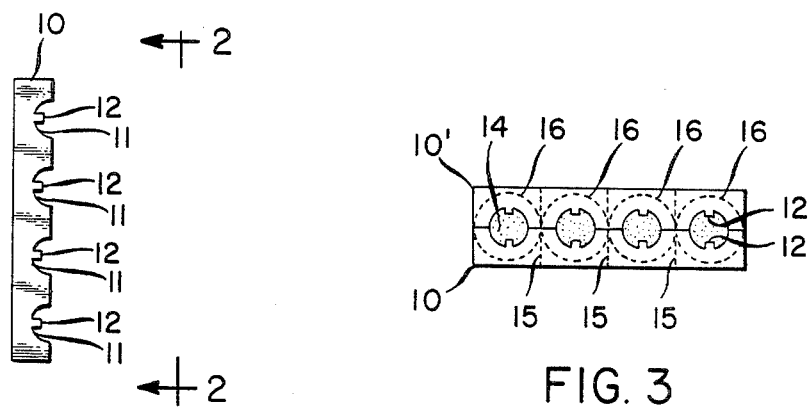
FIG. 1
FIG. 3
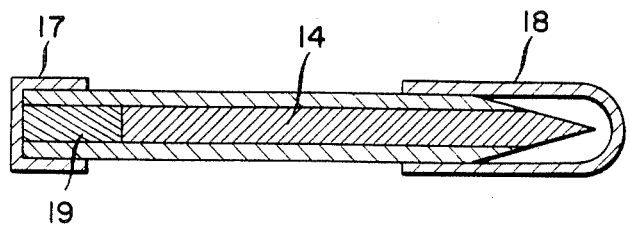
FIG. 4

METHOD FOR MAKING COSMETIC PENCILS

This is a continuation-in-part of our prior U.S. application, Ser. No. 296,386, filed Aug. 26, 1981, now U.S. Pat. No. 4,383,875.

This invention relates to cosmetic pencils, such as eye shadow, eye liner, lipstick, and the like. More particularly this invention relates to cosmetic pencils wherein the cosmetic composition is solvent-based.

Prior-art methods for forming cosmetic pencils, merely enclose a cosmetic lead in wooden slats, without special pretreatment. These prior-art methods are not satisfactory for solvent-based systems, because the leads tend to be weak and the solvent evaporates, rendering the finished product unacceptable.

The present invention, which overcomes these problems, comprises a method for forming a cosmetic pencil having a lead of solvent-based cosmetic composition comprising at least one wax or resin, solvent for the wax or resin, and pigment comprising the steps of:
  (a) packaging said lead in an airtight container and storing the packaged lead at a temperature below approximately 0° C. for approximately 12 to 168 hours, thereafter
  (b) storing the packaged lead at room-temperature for at least 2 hours, thereafter
  (c) removing said lead from said airtight container,
  (d) providing a pair of slats having grooves surfaces, said grooves upon joining of said surfaces forming a channel having inside dimension slightly larger than an outside dimension of said lead,
  (e) forming an assembly by inserting said lead into a groove and attaching said grooved surfaces to each other by adhesive bonding such that said lead is in said channel, and thereafter
  (f) wrapping said assembly with airtight wrapping such that said wrapping covers at least a portion of the outer surface of said assembly.

The term "solvent-based cosmetic composition" is intended to mean a cosmetic composition containing at least one wax or resin and a solvent for the wax or resin. Solvent-based cosmetic compositions useful in this invention are disclosed in U.S. Pat. Nos. 3,088,876 (May 1963, Buth) and 3,211,618 (Oct. 1965, Kambersky). Another composition for use with the present method contains:
9 percent Cantelilla wax;
15 percent $C_{18-36}$ acid triglyceride;
4 percent microcrystalline wax;
25 percent petroleum distillate;
18.2 percent cosmetically acceptable oil;
0.5 percent preservatives and antioxidants, and;
28.3 percent pigments.

The term "lead" is intended to mean the pencil's core made of cosmetic composition.

BRIEF DESCRIPTION OF THE DRAWINGS

FIG. 1 is an end view of a slat having a plurality of grooves.

FIG. 2 is a view of the slat of FIG. 1 along the lines 2—2.

FIG. 3 is an end view of two slats attached at matching surfaces.

FIG. 4 is a longitudinal sectional view of a finished pencil made in accordance with the invention.

DETAILED DESCRIPTION OF THE INVENTION

A solid lead made of a solvent-based cosmetic composition by techniques well known in the art is provided. Preferably the lead will be cylindrically shaped having round or elliptical cross section with diameter of 1/10" to ½", more preferably about ¼".

The lead must be packaged in an airtight container and stored at temperatures below approximately 0° C. for approximately 12 to 168 hours. The preferable storage temperature and time are 0° C. to −15° C. for 12 to 24 hours. This step may be accomplished by layering a plurality of leads in a single box lined by a 2 mil thick low density polyethylene bag and sealing the bag. The box containing the sealed bar is then placed in a freezer at the appropriate temperature for the appropriate time.

The packaged lead is then removed from the freezer and allowed to stand at room temperature (i.e. from about 20° to 28° C.) for at least 2 hours.

The lead is then removed from the airtight container in preparation for the next step. The unpackaged lead must not be allowed to stand in the open too long, or at least part of the solvent will evaporate.

A pair of slats, preferably wooden, having grooved surfaces is provided. The matching surfaces, when joined must form a channel having inside dimension slightly larger than the outside dimension of the lead.

It is preferable to provide slats having a plurality of matching grooves as illustrated in FIGS. 1 and 2. Slat 10 has longitudinal grooves 11 in the top surface shown in FIG. 2. Preferably each groove has a longitudinal ridge 12 about 0.01" deep to help hold the lead tightly during prolonged storage and use. The grooves (excluding the ridges) have inside dimension slightly larger than the outside dimension of the lead. For example, if the leads are circular having radius of 0.125", the radius of the groove may be from 0.003" to 0.010" larger than 0.125". A second slat 10' (see FIG. 3), preferably identical to slat 10, is provided. The two slats have identically spaced grooves, i.e., have matching grooves.

An assembly as in FIG. 3 is formed by attaching the matching surfaces to each other such that a lead is in each channel. For the slats illustrated in FIG. 3, this can be done by lightly coating at least one matching surface, such as the top surface and grooves of slats 10 with glue, such as a water dispersion of ethylene-vinyl acetate copolymer. Leads 14 are then placed in grooves 11 and second slat 10' is attached, forming the assembly of FIG. 3. A wooden plug 19 (see FIG. 4) may be placed in one end of the grooves. The slats are held together until the glue dries; preferably for at least 4 hours.

To form cylinder-shaped assemblies, each of which contains a single lead, the slats are rounded along lines 16 (see FIG. 3) and then cut into single-lead assemblies along line 15.

Preferably no more than 24 hours after the single-lead assemblies have been framed, they are wrapped with airtight wrapping such that the wrapping covers at least a part of the outer surface of the assembly. This is preferably accomplished by coating the lateral surface of the assemblies with clear varnish, allowing the varnish to dry and wrapping the coated surface with 1.5 mil thick metallized Mylar. The Mylar may be adhered to the pencils by pressure sensitive adhesive. The mylar may be preprinted with the manufacturer's trademark, the cosmetic type and color, etc.

One end of the wrapped pencils may then be capped with an airtight cap, element 17 of FIG. 4.

If it is desirable to point the pencils, they are stored in a cooler at 5° C. to −15° C., preferably 0° C. to −5° C. for 2 to 20 hours. The pencils are then removed from the freezer and pointed while they are still cold. After pointing, the pencils are fitted with an airtight metal point protector, element 18 of FIG. 4.

The completed pencils may now be stored at room temperature for prolonged periods without deterioration of the cosmetic composition.

The method of the present invention has the following advantages over prior-art systems:

1. There is very little solvent evaporation.
2. The leads are stronger, i.e., have a better structure.

Leads strengthened in accordance with the invention have uses other than for forming pencils. For example, such leads may be packaged in well known swivel or "push-up" containers frequently used for lipsticks and eye cosmetics in the past. See, for example, U.S. Pat. Nos. 3,106,908 and 2,419,526 which are incorporated herein by reference. To prevent premature evaporation of solvent, it is preferred that such containers be airtight.

What is claimed is:

1. A method for strengthening a cosmetic lead of solvent-based cosmetic composition comprising at least one wax or resin, solvent for said wax or resin, and pigment, comprising the steps of:
   (a) packaging said lead in an airtight container
   (b) storing said packaged lead at a temperature below approximately 0° C. for approximately 12 to 168 hours, thereafter
   (c) storing the packaged lead at room-temperature for at least two hours, and thereafter
   (d) removing said lead from said airtight container.

2. The method of claim 1, wherein said lead is cylindrical having a diameter of approximately 1/10 to ½ inches.

3. The method of claim 2, wherein said solvent based composition comprises candelilla wax, $C_{18-36}$ acid triglyceride, microcrystalline wax, petroleum distillate, cosmetically acceptable oil and pigment.

4. The method of claim 3 wherein said storage Step (b) is accomplished within a temperature range of approximately 0° to −15° C. for approximately 12 to 24 hours.

5. A cosmetic lead strengthened by the method of claim 4.

6. The cosmetic lead of claim 5 wherein said cosmetic composition is an eyeshadow.

7. A cosmetic lead strengthened by the method of claim 1.

* * * * *